United States Patent [19]

Guerrato et al.

[11] Patent Number: 4,908,470

[45] Date of Patent: Mar. 13, 1990

[54] PROCESS FOR THE METHYL-4-(DIMETHYLAMINO)-3,5-DIMETHOXYBENZOATE

[75] Inventors: Alfredo Guerrato, Trissino, Italy; Martin Karpf, Reinach, Switzerland; Hanny K. Berger, Aesch, Switzerland; Ivan Kompis, Oberwil, Switzerland; Markus Schlageter, Bottmingen, Switzerland

[73] Assignee: Hoffman-La Roche Inc., Nutley, N.J.

[21] Appl. No.: 278,058

[22] Filed: Nov. 30, 1988

[30] Foreign Application Priority Data

Dec. 3, 1987 [CH] Switzerland ............... 4720/87

[51] Int. Cl.$^4$ ............................................ C07C 101/48
[52] U.S. Cl. ........................................ 560/46; 562/453; 544/325
[58] Field of Search ................. 560/46; 562/453; 544/325

[56] References Cited

U.S. PATENT DOCUMENTS

| 3,775,464 | 11/1973 | Pifferi | 560/46 |
| 3,801,636 | 4/1974 | Horrom et al. | 564/163 |
| 4,008,236 | 2/1977 | Perun et al. | 544/325 |
| 4,515,948 | 5/1985 | Kompis et al. | 544/325 |

FOREIGN PATENT DOCUMENTS

| 0280975 | 7/1988 | European Pat. Off. |
| 0913938 | 3/1982 | U.S.S.R. | 560/46 |

Primary Examiner—Bruce D. Gray
Attorney, Agent, or Firm—George M. Gould; Bernard S. Leon; William G. Isgro

[57] ABSTRACT

Methyl 4-dimethylamino-3,5-dimethoxybenzoate, an intermediate in the preparation of the antibacterially active aditoprim, is obtained from 4-amino-3,5-dibromobenzoic acid by replacement of the bromine atoms by methoxy groups and subsequent methylation.

2 Claims, No Drawings

PROCESS FOR THE METHYL-4-(DIMETHYLAMINO)-3,5-DIMETHOXYBENZOATE

BRIEF SUMMARY OF THE INVENTION

The invention relates to a process for the preparation of methyl 4-(dimethylamino)-3,5-dimethoxybenzoate which can be utilized as an intermediate for the manufacture of 2,4-diamino-5-(3,5-dimethoxy-4-dimethylamino)benzylpyrimidine (aditoprim).

DETAILED DESCRIPTION OF THE INVENTION

The invention relates to a process for the preparation of methyl 4-(dimethylamino)-3,5-dimethoxybenzoate which can be utilized as an intermediate for the manufacture of 2,4-diamino-5-(3,5-dimethoxy-4-dimethylamino)benzylpyrimidine (aditoprim).

For the economical utilization of aditoprim, especially in the field of veterinary medicine, the high costs for preparing said compound have hitherto been an obstacle when known processes such as, for example, the process described in DE Patent Specification No. 2 443, 682 had to be used.

By the process of the invention, aditoprim can be prepared with substantially more economical costs than has been possible with the known processes. This result is achieved by the discovery of a process in which p-aminobenzoic acid is brominated to 4-amino-3,5-dibromobenzoic acid, the latter is converted to 4-amino-3,5-dimethoxybenzoic acid and, thereafter, methylated to methyl 4-(dimethylamino)-3,5-dimethoxybenzoate. The latter compound can be reduced to 4-(dimethylamino)-3,5-dimethoxybenzaldehyde which can be converted into aditoprim in a known manner. When conventional procedures are used, the conversion of the 4-amino-3,5-dibromobenzoic acid and the subsequent methylation of the 4-amino group encounter difficulties such as unsatisfactory yields and the formation of larger amounts of undesired by-products.

It has now been found that the replacement of the bromine atoms by methoxy groups proceeds in surprisingly good yield when 4-amino-3,5-dibromobenzoic acid is reacted with an alkali methylate such as sodium methylate in the presence of cuprous oxide ($Cu_2O$) and dimethylformamide or dimethylacetamide. Furthermore, it has been found that the methylation of the thus-obtained 4-amino-3,5-dimethoxybenzoic acid by means of dimethyl sulfate in the presence of a base, for example, an alkali carbonate or hydrogen carbonate, such as, potassium carbonate or sodium hydrogen carbonate, proceeds in surprisingly high yield when a lower aliphatic or cycloaliphatic ketone is used as the solvent.

The process in accordance with the invention for the preparation of methyl 4-(dimethylamino)-3,5-dimethoxybenzoate is characterized by reacting 4-amino -3,5-dibromobenzoic acid with an alkali methylate in the presence of $Cu_2O$ and dimethylformamide or dimethylacetamide to give 4-amino-3,5-dimethoxybenzoic acid and methylating this product with dimethyl sulfate in the presence of a base in a lower aliphatic or cycloaliphatic ketone while heating.

In the first process step about a molar amount of $Cu_2O$, based on the starting material, 4-amino-3,5-dibromobenzoic acid, is used. Sodium methylate in methanol, conveniently in a large excess, for example, in up to 10-fold molar excess, based on the starting material, is preferably used as the alkali methylate. Furthermore, the dimethylformamide or the dimethylacetamide is added in large excess, for example, in about 10- to 20-fold molar amount, based on the starting material Dimethylformamide and dimethylacetamide act as acylating agents, whereby the intermediately-formed N-formyl or N-acetyl group is cleaved off in the basic medium in the course of the working-up of the reaction mixture. The reaction is carried out while heating Conveniently, heating is carried out up to the boiling point of the reaction mixture and the majority of the solvent is removed by distillation at atmospheric pressure. For the working-up. the residue is heated with alkali, for example, sodium hydroxide solution and filtered. The filtrate is acidified (PH 5-6) and the product is isolated by filtration or extraction with a suitable solvent, washed and dried.

In the second process step, the 4-amino-3,5-dimethoxybenzoic acid is methylated with dimethyl sulfate in the presence of a base. preferably potassium carbonate. The methylating agent is conveniently used in about a stoichiometric amount. Acetone, ethyl methyl ketone, isopropyl methyl ketone, isobutyl methyl ketone and cyclohexanone are examples of lower aliphatic and cycloaliphatic ketones which can be used as the solvent in this step. Acetone and ethyl methyl ketone are preferred. The reaction temperature conveniently is in the range of from about 50° to about 70° C. The reaction mixture can be worked-up in the usual manner, for example, by extraction.

The examples which follow further illustrate the invention. Temperatures are in degrees Centigrade unless otherwise stated.

EXAMPLE 1

Preparation of 4-amino-3,5-dimethoxybenzoic acid 258 g of copper(I) oxide and 1670 ml of sodium methylate solution (30% in methanol) were boiled at reflux (88°–93° C.) for 15 minutes while stirring and gassing with argon. At this temperature, there was added dropwise with simultaneous distillation a solution consisting of 531 g of 3,5-dibromo-4-aminobenzoic acid, 1670 ml of sodium methylate solution (30% in methanol) and 2700 ml of dimethylformamide (dried over molecular sieve). The solvent was subsequently further distilled. 2200 ml were distilled off in total. The resulting red suspension was stirred at 113°–114° C. for an additional 45 minutes. Thereafter, 1300 ml of dimethylformamide were distilled off in a water-jet vacuum. 7500 ml of 4N sodium hydroxide solution were added to the resulting red residue and the suspension was stirred at about 100° C. for 30 minutes. Thereby 800 ml were again distilled off. The hot suspension was suction filtered over an internal glass suction filter. The residue was suspended three times in 1800 ml of hot water and filtered off each time. The solution, cooled to 5° C., was adjusted to PH 5 with 2000 ml of acetic acid while stirring. The resulting brown suspension was suction filtered and the residue was washed with 1000 ml of ice-water. The residue was dried at 60° C. in a water-jet vacuum. The thus-obtained crude product was boiled up with 3200 ml of methanol. The brown suspension was suction filtered and the filtrate was evaporated to dryness. There were obtained 313 g (88%) of 4-amino-3,5-dimethoxybenzoic acid.

EXAMPLE 2

Preparation of 4-dimethylamino-3,5-dimethoxybenzoic acid 100 g of 4-amino-3,5-dimethoxybenzoic acid and 223 g of potassium carbonate were heated to 70° C. in 201 g of ethyl methyl ketone while stirring and treated with 15.2 ml of dimethyl sulfate. The reaction mixture was heated to reflux temperature (~80° C.) and stirred at this temperature for 1 hour. Thereafter, 10 ml of acetic acid were added. The reaction mixture was stirred at ~80° C. for an additional 30 minutes, cooled to 50° C. and filtered. The residue was washed with 200 ml of ethyl methyl ketone (50° C.) and the combined filtrates were evaporated. There were obtained 117 g of crude product which, crystallized from a 6-7-fold amount of methanol/water (1:1) with the action of 10 g of charcoal yielded 95-100 g (79-84%) of 4-dimethylamino-3,5-dimethoxybenzoic acid melting point 65°-69° C.

EXAMPLE 3

Preparation of 4-dimethylamino-3,5-dimethoxybenzoic acid methyl ester 10 g of 4-amino-3,5-dimethoxybenzoic acid and 24,5 g Potassium carbonate were heated to 50° in 65 ml of acetone and treated with 17 ml of dimethylsulfate. The reaction mixture was stirred for 5 hours at this temperature, cooled to 30° and treated with 50 ml of water and subsequently 80 ml of 10% hydrochloric acid. The reaction mixture was extracted three times with 100 ml each of isopropyl acetate. The aqueous phase was adjusted to pH 9 by the addition of 4 ml of 28% sodium hydroxide solution and extracted three times with 100 ml each of ispropyl acetate. The organic phase was washed two times with 100 ml each of water, dried with magnesium sulfate and concentrated. The crude product (14 g) was recrystallized from 150 ml of hexane and yielded 8,8 g (73%) of 4-dimethylamino-3,5-dimethoxybenzoic acid methyl ester. melting point 725°-74°.

We claim:

1. A process for the preparation of methyl 4-(dimethylamino)-3,5-dimethoxybenzoate which comprises reacting 4-amino-3,5-dibromobenzoic acid with an alkali methylate in the presence of $Cu_2O$ and dimethylformamide or dimethylacetamide, and methylating the resulting 4-amino-3,5-dimethoxybenzoic acid with dimethyl sulfate in the presence of a base selected from the group consisting of lower aliphatic ketone and cycloaliphatic ketone, while heating, to yield methyl 4-(dimethylamino)-3,5-dimethoxybenzoate.

2. A process according to claim 1, wherein the methylation is carried out in the presence of acetone or ethyl methyl ketone.

* * * * *